(12) United States Patent  
Hanft (10) Patent No.: US 9,201,413 B2  
(45) Date of Patent: Dec. 1, 2015

(54) PROTECTIVE PATIENT FOOTWEAR DESIGN AND MANUFACTURING SYSTEM AND METHODS

(71) Applicant: Jason R. Hanft, South Miami, FL (US)

(72) Inventor: Jason R. Hanft, South Miami, FL (US)

(*) Notice: Subject to any disclaimer, the term of this patent is extended or adjusted under 35 U.S.C. 154(b) by 355 days.

(21) Appl. No.: 13/804,268

(22) Filed: Mar. 14, 2013

(65) Prior Publication Data

US 2014/0277658 A1    Sep. 18, 2014

(51) Int. Cl.
| | | |
|---|---|---|
| *A61B 5/103* | (2006.01) | |
| *A61B 5/07* | (2006.01) | |
| *A43D 1/02* | (2006.01) | |
| *G05B 15/02* | (2006.01) | |
| *G05B 19/42* | (2006.01) | |
| *A43B 7/14* | (2006.01) | |
| *A43B 7/28* | (2006.01) | |

(52) U.S. Cl.
CPC ............. *G05B 15/02* (2013.01); *A43B 7/141* (2013.01); *A43B 7/28* (2013.01); *G05B 19/4207* (2013.01); *A43D 2200/60* (2013.01); *G05B 2219/35036* (2013.01); *G05B 2219/45243* (2013.01)

(58) Field of Classification Search
CPC ........ A61B 5/103; A61B 5/107; A43D 1/025; A43D 3/021; A43D 2200/60; A43D 1/02; G05B 2219/45243
USPC .......................................................... 700/95
See application file for complete search history.

(56) References Cited

U.S. PATENT DOCUMENTS

| | | | |
|---|---|---|---|
| 4,745,290 A | | 5/1988 | Frankel et al. |
| 5,195,030 A | * | 3/1993 | White .................. 705/27.2 |
| 5,339,252 A | | 8/1994 | White et al. |
| 5,611,153 A | | 3/1997 | Fisher et al. |
| 6,315,786 B1 | | 11/2001 | Smuckler |
| 6,463,351 B1 | * | 10/2002 | Clynch ............ A61F 2/5046 623/901 |
| 7,206,718 B2 | * | 4/2007 | Cavanagh et al. ........ 702/155 |
| 7,409,256 B2 | | 8/2008 | Lin et al. |
| 7,493,220 B2 | * | 2/2009 | Leigh et al. ................ 702/56 |
| 7,661,170 B2 | | 2/2010 | Goode et al. |
| 7,926,363 B2 | * | 4/2011 | Miller .................. A43B 7/141 73/862.041 |
| 8,005,558 B2 | * | 8/2011 | Waatti et al. ................. 700/98 |
| 8,596,145 B2 | * | 12/2013 | Miller et al. .......... 73/862.041 |
| 2001/0020222 A1 | | 9/2001 | Lee et al. |

(Continued)

FOREIGN PATENT DOCUMENTS

| | | |
|---|---|---|
| CN | 20071119279 | 12/2007 |
| JP | 2001204512 | 7/2001 |

OTHER PUBLICATIONS

U.S. Appl. No. 61/739,346, filed Dec. 2012, Wawrousek et al.*

(Continued)

*Primary Examiner* — Ronald Hartman, Jr.

(74) *Attorney, Agent, or Firm* — Akerman LLP; Richard P. Gilly (57) ABSTRACT

This disclosure relates to a design and manufacturing system for protective patient footwear, as well as related methods. The system includes suitable hardware, software, and related peripherals, which function to acquire data related to the patient's particular footwear needs, such as by three-dimensional scanning. A design subsystem interfaces with the inputted data to permit the resulting design to reflect particular foot conditions in the design and subsequent manufacturing process. A manufacturing subsystem receives the resulting design and includes hardware and software to manufacture the protective patient footwear.

15 Claims, 3 Drawing Sheets

(56) References Cited

U.S. PATENT DOCUMENTS

| | | |
|---|---|---|
| 2002/0120531 A1 | 8/2002 | Fonsen |
| 2002/0158358 A1 | 10/2002 | Franzene |
| 2004/0133431 A1* | 7/2004 | Udiljak .................. A43B 7/141 705/26.1 |
| 2004/0168329 A1 | 9/2004 | Ishimaru |
| 2005/0049816 A1* | 3/2005 | Oda et al. ...................... 702/127 |
| 2005/0171456 A1* | 8/2005 | Hirschman .......... A61B 5/1036 600/592 |
| 2006/0143839 A1 | 7/2006 | Fromme |
| 2007/0038042 A1* | 2/2007 | Freeman et al. .............. 600/310 |
| 2007/0043582 A1* | 2/2007 | Peveto et al. ...................... 705/1 |
| 2007/0282562 A1* | 12/2007 | Schwartz et al. ............. 702/139 |
| 2008/0010856 A1* | 1/2008 | Hakkala ............................ 36/43 |
| 2008/0104778 A1 | 5/2008 | Drake et al. |
| 2008/0189194 A1* | 8/2008 | Bentvelzen ...................... 705/27 |
| 2010/0130830 A1* | 5/2010 | Lin ...................... A61B 5/0064 600/300 |
| 2010/0275461 A1 | 11/2010 | Cook et al. |
| 2011/0082578 A1 | 4/2011 | Stanhope et al. |
| 2011/0099845 A1 | 5/2011 | Miller |
| 2014/0182170 A1* | 7/2014 | Wawrousek ............. A43B 5/02 36/103 |
| 2015/0101134 A1* | 4/2015 | Manz et al. ................. 12/142 R |

OTHER PUBLICATIONS

Piller, "Footwear Customization 3.0: The First Rapid Manufactured Shoe," Oct. 24, 2006, http://mass-customization.blogs.com/mass_customization_open_i/2006/10/footwear_custom.html, pp. 1-3.

Tuck et al., "Rapid manufacturing facilitated customization," International Journal of Computer Integrated Manufacturing, pp. 245-258, vol. 21, Issue 3, 2008.

Patent Cooperation Treaty, "International Search Report and Written Opinion" Korean Searching Authority, document of 8 pages, Jul. 28, 2014.

* cited by examiner

PROTECTIVE PATIENT FOOTWEAR DESIGN AND MANUFACTURING SYSTEM AND METHODS

FIELD OF THE INVENTION

This disclosure relates to the automated design and manufacture of footwear, and in particular, to automated design and manufacturing systems for patients with foot or other orthopedic conditions requiring accommodation.

BACKGROUND

Current systems and methods for designing or manufacturing footwear for diabetics or other patients with podiatric or orthopedic needs are generally time consuming and antiquated. To the extent automation of footwear design or manufacturing has occurred, such systems and methods suffer from various drawbacks and disadvantages, and are not well-suited for the particular needs of diabetics and other patients with podiatric or orthopedic issues.

SUMMARY

This disclosure relates to a design and manufacturing system for protective patient footwear, as well as related methods. The system includes suitable hardware, software, and related peripherals, which function to acquire data related to the patient's particular footwear needs, such as by three-dimensional scanning. A design subsystem interfaces with the inputted data to permit the resulting design to reflect particular foot conditions in the design and subsequent manufacturing process. A virtual last creation subsystem may be included to process the design parameters received by the system. The virtual last subsystem may then generate output for use in producing, for example, by subsequent manufacture, a corresponding custom shoe, brace, boot, casts or other corrective footwear for use in at-risk patients, such as diabetics.

In one possible version, the data generated by the virtual last would in turn be input into an automated tool for fabricating the footwear. One such automated tool would be computer-driven manufacturing tool. The tool is programmable to create footwear using any suitable manufacturing techniques, including injection molding techniques or three-dimensional printing techniques, and could thereby be used to create a custom, accurate product. The materials used for the resulting custom footwear may include, but not be limited to: open and closed cell foams, hybrid foam, EVA, cyanoacrylates, low friction cloth, Gore-tex, neoprene, rubber, plastics, paper, steel and carbon fiber. Quality and accuracy of the final product will be digitally compared to the original scan to validate accuracy of the final product.

In one implementation, the design and manufacturing system for protective patient footwear comprises distinct subsystems, and suitable physical and logical interconnections between such subsystems to integrate the scanning, design, and manufacturing steps in an efficient manner. The subsystems and related interfaces may be designed so that they are interchangeable and thus adaptable to different retail and office environments, as regards input of the design, and can likewise be interchangeable with different CAD or CAM software subsystems in connection with the generation of the virtual last and subsequent manufacture. As such, the system of the present disclosure may be based, at least partially, on commercially available 3-D scanning systems, as well as commercially available CAD/CAM systems and mold making and injection molding subsystems. The foregoing systems, however, are adapted and modified to not only integrate and streamline the process of procuring customized footwear for patients' foot conditions, but also the systems are able to accommodate particular foot conditions in a straightforward manner either in response to detection of such conditions or suitable input from medical practitioners during the design process.

When the system is configured to generate a virtual last prior to manufacturing, then the customized or particular needs are reflected in the generation of the virtual last. In other configurations, the customized or particular needs may be data output to the computer-driven manufacturing system, in those cases where a virtual last is not part of the system. Regardless of the exact system configuration, the disclosed system is able to accommodate the particular needs or conditions identified during consultation, scanning or other interaction with any number of medical practitioners or professionals, in a straightforward manner, and in turn allows for the ultimate manufactured footwear to address such needs or conditions.

DESCRIPTION

Figure 1:
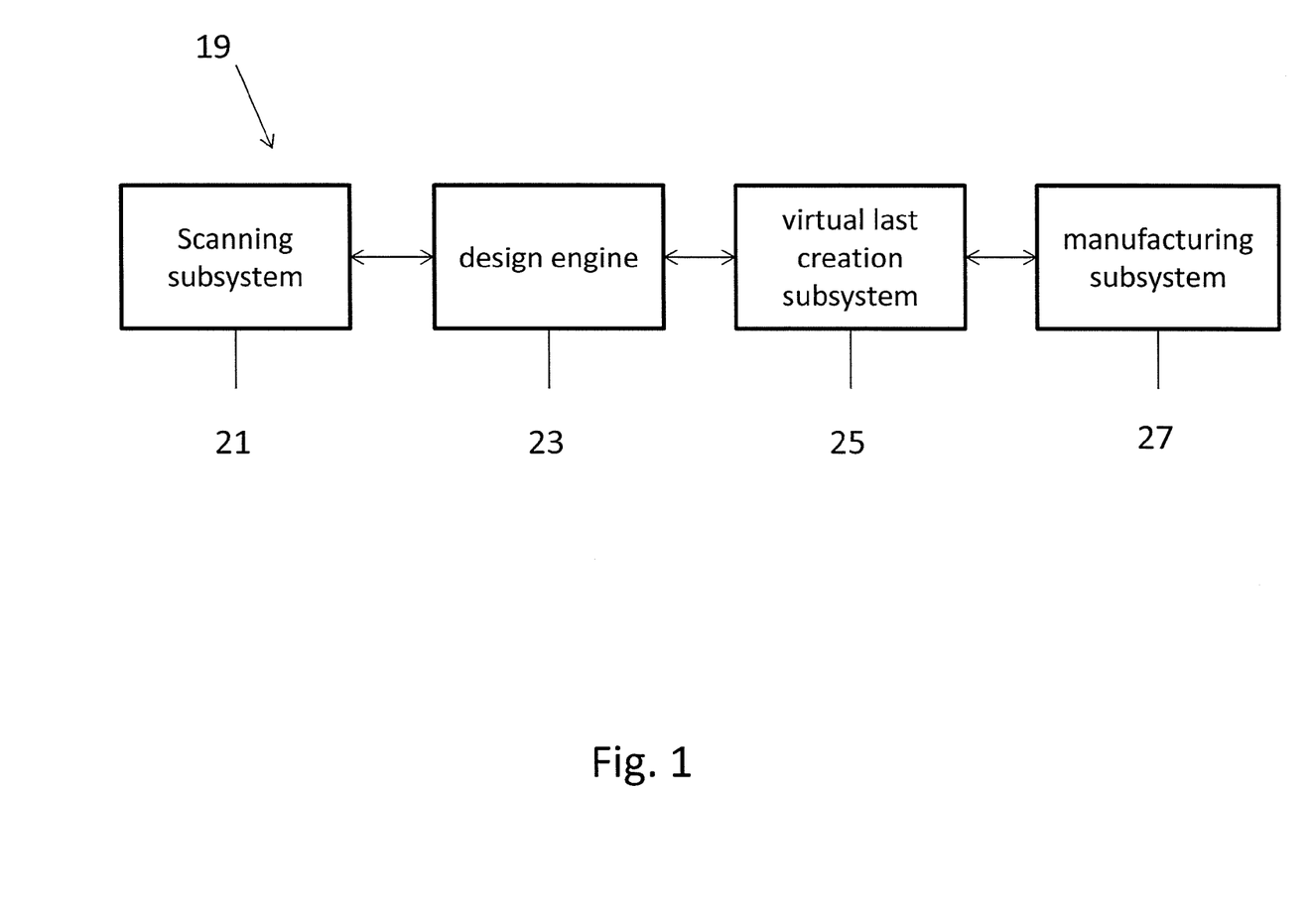
FIG. 1 is a schematic of one possible implementation of the present disclosure.

One possible implementation of a design and manufacturing system for protective patient footwear 19 is shown in FIG. 1. Scanning subsystem 21 receives suitable input related to a patient's foot or ankle. The scanning subsystem makes use of a suitable user interface so that it can be used by the medical practitioner, whether a medical technician, orthotists, pedorthist, orthopedist, podiatrist, or any number of other medical practitioners concerned with foot conditions and disease. The user interface and other hardware and software of the scanning subsystem may be varied to suit the particular environment where it is located, whether office, hospital, retail, ambulatory center, or other suitable venue.

Scanning subsystem 21 includes a scanner 22, such as a three-dimensional scanner for patient(s) lower extremities, or a similar device for detecting dimensions or other information related to the patient's lower extremities, gait, or other conditions under examination, or for otherwise receiving such inputs. The data generated by scanning subsystem 21 is further processed by a design engine, such as a podiatric design engine 23, which accounts for podiatric or other foot conditions. It will be appreciated that while design engine 23 is referred to as "podiatric," the system disclosed herein is not intended to be limited to podiatric professionals, but may likewise be suitable for many other medical practitioners who are called upon to provide individuals with suitable footwear to address foot conditions. As such, any practitioners dealing with conditions of the foot, regardless of title, specialty, or experience, may make use of this system, including the corresponding podiatric design engine 23, in order to have the design reflect the recommendations of such foot care practitioners.

In addition, the protection, accommodation, or other compensating features of the design may be generated at any number of points relative to the scanning process. In other words, the system may include suitable programming for the medical practitioner to input abnormalities or other data used to modify shoe and insole design and construction prior to the scan, to thereby create a suitable spreadsheet or other data structure accessible by the system in subsequent phases of operation. Furthermore, the digital scanning subsystem 21 itself may include suitable programming to detect abnormalities or other conditions requiring accommodation and either generate a default accommodation in subsequent design phases, or "flag" conditions for consideration through the user interface to the medical practitioner, so that design alterations can be considered. In still other implementations, suitable inputs related to the patient conditions which need to be accommodated can be received subsequent to the three-dimensional scan. For example, data input about foot conditions can likewise be received through the design engine 23, or any other suitable input means associated with either the scanner or other modules of the system.

Regardless of when the patient particulars are received by system 21, system 21 can include suitable programming to automatically alter certain corresponding aspects of the design, or present suggested alterations to the medical practitioner through a suitable graphical user interface. In one version of the system, design engine 23 may be configured to include suitable software programming to allow for the accommodation of any number of dermatologic, orthopedic, neurologic, biomechanical, and surgical conditions in the resulting footwear design. Modification of such design and the corresponding custom construction therefore can address findings of the medical history input into the system, as well as parameters relating to the scanning or other physical exam findings. Dermatological parameters such as wounds, calluses, fissures, high pressure areas, at-risk areas, fat pad atrophy, tissue loss, excess tissue, and scars may be the subject of suitable programming, so that upon detection of, or input related to, these conditions, modifications to the corresponding design, virtual last or ultimately the footwear to be fabricated are incorporated into the operations of system 19. Similarly, orthopedic or neurological conditions may be the subject of suitable programming in the system, including neural functions and muscle functions, particular positions of hips, knees, ankles, and the subtalar joint. Range of motion of hips, knees, ankles, and subtalar joints, as well as the range of motion of greater and lesser metatarsophalangeal joints, proximal and distal inter-phalangeal joints—any or all such conditions may be received as input into the system through suitable programming, and may be factored into design recommendations or the ultimate design of the particularized footwear. Still further, foot position and geometry, whether related to the ankle, rear foot, mid-foot, forefoot, or digits may be scanned, input, or otherwise reflected in the operation of design subsystem 23.

The system may also include suitable programming to allow for accommodation of surgical conditions. For example, surgeries related to the hips, knees, ankles, tendons, amputations, thigh, tibia, fibula, related joints, and of course, the foot, as well as vascular or other effects of such surgeries, such as arterial bypass, vein surgery, or stents, on the proposed footwear—any or all may be inputted or detected by suitable programming in design subsystem 23.

It will be appreciated that any number of additional factors may be the subject of suitable programming, hardware, or peripherals in the design subsystem, such that corresponding accommodations, as judged appropriate or suitable, may be made to the design and resulting footwear. So, as an example, system 19 may include additional hardware to analyze biomechanical factors, such as motion detectors, accelerometers, or any number of sensors, along with corresponding programming, adapted to provide suitable data for use in the footwear design.

System 19 may include suitable programming to accommodate a prior amputation of the great toe, as just one example of the sorts of conditions which can be accommodated. One possible approach would be for system 19 to receive either prior to scanning, during scanning or otherwise input data specific to the level of amputation involved, as well as the effect of the amputation on foot function, the dermatological condition of the amputation site, and a biomechanical evaluation and gait analysis. These latter two factors may either be detected by suitable motion detectors associated with the system or input through a suitable user interface by the medical practitioners (or both), and suitable programming will be devised in response to such inputs to reflect the missing tissue or functional alterations in the corresponding design. Among possible accommodations which the system can be programmed to make would be the addition of insole materials to fill voids for the missing tissue. Such operations could be contemplated in three dimensions at the design stage and in the corresponding manufacturing stage discussed subsequently. The system programming may have a default or various suggestions for filling the void based on information collected.

Another possible accommodation from such amputation would be the addition of materials under the remaining portions of the foot to account for additional pressure and forces that are transferred due to the amputation. Again, suitable programming can either respond to the detection of the amputation or the input of information corresponding to such amputation, and alter the scanned data accordingly or alter any of the other information used to determine the amount of material under the foot. System programming may likewise suggest a default to the addition of material to the insole to protect the residual portion of the first metatarsal from increased or abnormal forces.

In response to the detection of, or input related to, gait abnormality, suitable programming may alter scanned data or otherwise result in the provision of materials both in the insole and in the ultimate shoe construction. For example, in such situations, the medial portion of the insole underlying the filler for the missing digit could be stiffened with a harder or mixed density material. Different types of material might also be suggested by the system in response to detection or input of a gait abnormality, so as to transfer weight and achieve better balance across a patient's remaining foot surface. Programming may also modify or suggest modification to the insole and outsole of the shoe to accommodate for abnormal forces from such amputations.

Still further, the mechanical characteristics of the midsoles and outsoles themselves may be modified by the system programming in response to data received relating to gait abnormality of the prior amputation. Such modification would increase the flexibility in the area of the metatarsal-phalangeal joints, so as not to increase the forces or weight bearing load on the remaining function of the foot.

The system may be suitably programmed to not only alter scanned data or the associated design in response to foot conditions, but to do so in a manner that does not alter the external appearance of the shoe from that "normally" expected—in other words, so that to the outside observer, there is no aesthetic indicator of the underlying deformity or modifications.

The system may also be programmed to accommodate into design and manufacture a prior history of ulceration or a wound in the plantar surface of the second metatarsal-phalangeal joint. One approach would be to allow the medical practitioner to input historical information related to ulceration or wounds in a series of interrelated fields in a suitable user interface. As such, the system is programmed to identify and detail the etiology and location of the prior wound or ulceration. For such conditions, the system may likewise have suitable input programming so that foot function is recorded through suitable input, dermatological conditions and scarring assessed, biomechanical and gait evaluations inputted, and other input relating to abnormalities or factors that either caused, or resulted from, the prior wound or ulceration. The system is programmed to quantitatively evaluate the nature and character of the inputs and thus use them as variables to alter the data or design arising from digital scanning, such alterations potentially accommodating the missing tissue, changes to the skin, and other functional alterations. Another possible approach to the situation of prior ulcerations and wounds would be for the system to be programmed to modify insole materials to accommodate missing tissue, loss of elasticity, or lack of impact absorption due to scarring and tissue loss.

The accommodation of ulceration and wounds to the plantar surface may also be programmed to suggest specific insole top cover materials to aid in friction reduction to the area at risk. Similarly, the shape and dimensions of the insole may be modified in response to wound data received in order to protect the prior wound site and the remainder of the foot.

The programming of the system may permit modifications to be done in three dimensions, using the factors relating to the prior history of ulceration and wounds, along with information collected from the scan. Again, the exact sequence of scanning, detection of, or inputs related to conditions requiring accommodation can be varied. For example, proposed or suggested accommodations may be input prior to scanning and factored into the subsequent scan, or the scanning may proceed first, with the resulting design receiving modifications or suggested modifications as a result of the detected or inputted abnormalities.

Programming may also be devised to alter material type and thickness in response to receiving input indicating a particular cause of the wound. Similar to the previous discussion on great toe amputation, the style, shape, and materials of the midsole may be revised to offload the previously wounded area and protect the remainder of the foot. In response to suitable wound or ulceration input, the system may suggest or automatically alter outsole material, including its design and functionality, so as to address the mechanics of the foot and protect from reinjury of the wound or ulceration.

As another example of customizing footwear to address foot conditions, the system may include suitable programming to accommodate an osseous deformity of the toes, so-called "hammer toes." In relation to scanning of the foot, as described in the previous examples, suitable programming will permit the detection or receipt of input of data related to digital position, associated muscle function, and gait analysis. The system may likewise allow foot function to be characterized with suitable inputs for subsequent processing, as well as dermatologic conditions of the toes, and the condition of the plantar skin—any or all such factors being suitably processed by the system, for example, by the design engine 21, in order to accommodate for the deformity. In the context of hammer toes, the system may include specific programming so that the size and shape of the forefoot noted from the scanned image is factored into the overall design. The noted forefoot dimensions may thus be processed by the system (i.e., the design engine 23), to automatically recommend or select particular materials for the top cover and vamp of the shoe to be manufactured, such materials selected for their properties to protect and provide space for the hammer toe deformity.

Similar programming of this system can accommodate the hammer toe deformity by automatically adjusting or making suggestions to adjust size, material, and shape of the insole as a function of the support, protection, and accommodation needed for digital contraction and changes to the associated dorsal and plantar skin. To the extent the hammer toe deformity causes mechanical and gait abnormalities, design engine 23 in particular, or the system in general, may be suitably configured to modify or suggest modifications to outsole design and shape, including increased flexibility, roller-rocker construction, fillers and pads, the use of shear reducing materials, friction reducing liners, and heat adaptable materials. As with the previous accommodations discussed, suitable programming to address the hammer toe deformity will allow for accommodations while maintaining the external appearance of the shoe, so that to the outside observer, there would be no aesthetic indicator of the underlying deformity.

As seen by the above examples and description, design engine 23 and the overall system 19 for designing and manufacturing protective patient footwear include a rich set of tools, features, and associated programming so that the many variables and possible accommodations to protect or accommodate a patient's foot condition can be efficiently orchestrated into a customized and suitable design to achieve therapeutic ends.

It would be appreciated that the interface through which foot conditions are input into the system may be varied to suit any number of applications. Checklists, menu-driven screens, and any number of automatic detection and scanning methodologies may be used to provide data associated with the patient's condition and the optimal or available design alternatives to address such conditions. The disclosed system has been programmed to suit the particular needs of foot specialists so as to design and manufacture the resulting protective footwear in a more straightforward fashion.

Having discussed the scanning subsystem 21 and design engine 23, and the various programming for generating associated footwear designs associated with the system and design engine 23, the present system 19 also may integrate computer-assisted manufacturing operations. So, for example, in the implementation illustrated in FIG. 1, a virtual last creation subsystem 25 may be included in system 19. The phrase "virtual last" is meant to refer to the electronic representation of a three-dimensional last used in connection with the making of corresponding footwear. In one implementation, the virtual last represents a typical "male" structure, and is used in subsequent automated manufacturing to correspond to the interior of the customized shoe, with materials being built to the outside of such last. Any number of other forms of virtual lasts are also contemplated, including a "female" mold inside of which would be built or manufactured the associated customized shoe. A combination of male and female molds may likewise be used either in conjunction with an injection molding process or as an intermediary to generate the required jigs or other forms associated with injection molding processes. In one implementation, virtual last creation subsystem 25 functions to perform computer-aided design and computer-aided manufacturing.

In still other implementations, it will be appreciated that virtual last creation subsystem 25 is optional, and that design engine 23 may programmed to generate the protective footwear design from suitable processing of the data received from the scanning subsystem 21. Still other arrangements of design functionality in one or more subsystems are possible, depending on the particular implementation.

In one implementation, the use of injection molding is such that the insole is integrated into the shoe, as opposed to being a separate piece which is fitted inside the footwear and thus prone to slippage or loss.

The exact exchange and formatting of data received by system 19, from the scanning of the foot to the generation of the virtual last, may occur with or without design engine 23. Depending on the implementation, manufacturing-ready output may be generated in the virtual last creation subsystem 25, the design subsystem 23, or even as early as the scanning subsystem 21. In other words, depending on the particular application, the data necessary to create the virtual last may be generated at any number of phases in the described system, whether it be scanning, design, or last creation.

The above-described system may include suitable computer-aided manufacturing functionality so that the virtual last may be used to fabricate the customized shoe as an end product. In one possible implementation, suitable output files are generated by one or more of the preceding subsystems 21, 23, or 25 of system 19 so that an injection molding process may be used to create the customized footwear. The use of injection molding may be used exclusively or in combination with other techniques. Such injection molding may be accomplished by manufacturing subsystem 27 shown schematically in FIG. 1.

Figure 2:
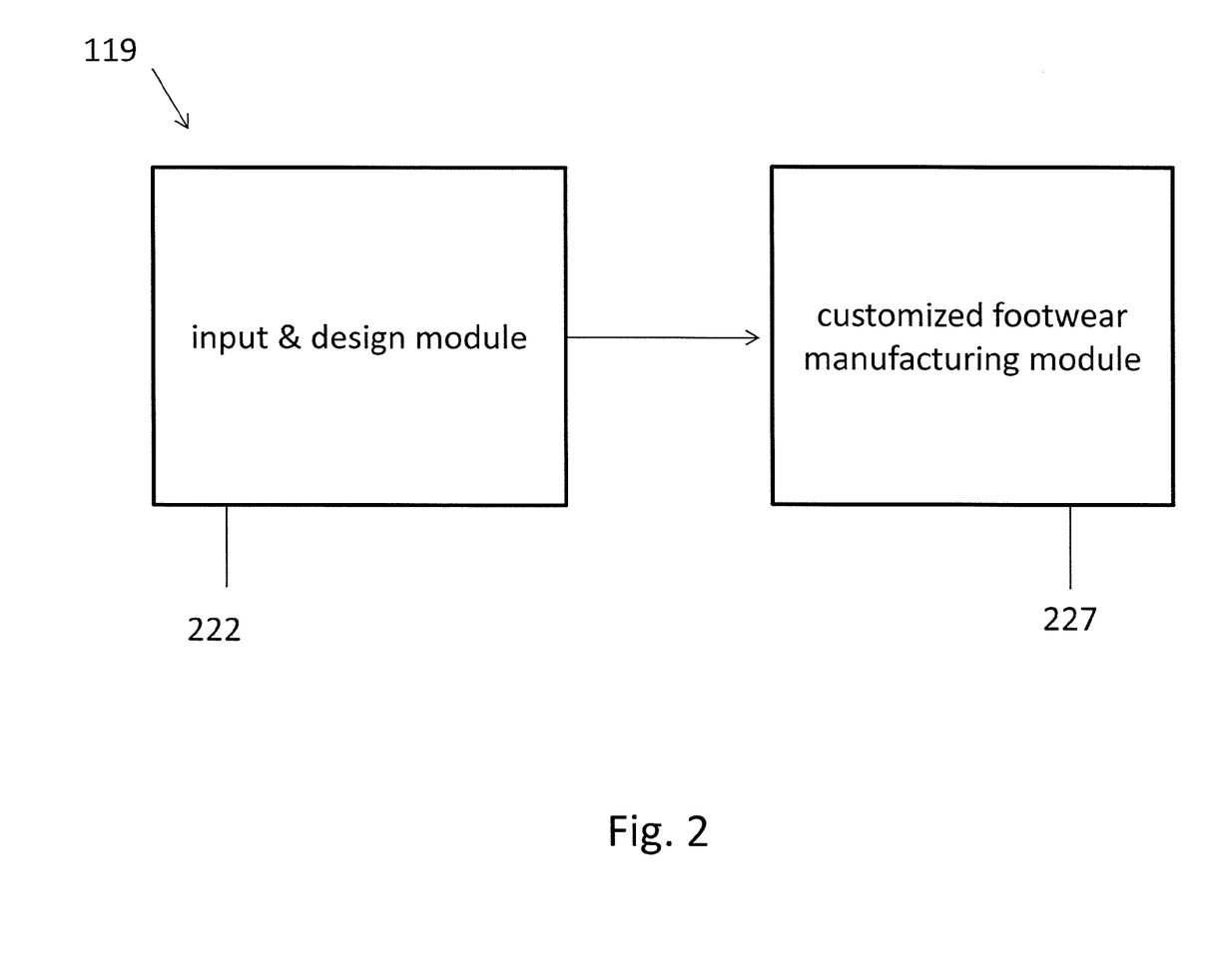
FIG. 2 is a schematic of another possible implementation of the present disclosure.

The exact dividing line between scanning subsystem 21, design subsystem or engine 23, virtual last creation subsystem or module 25, and the manufacturing subsystem 27 may vary depending on the particular application. It is also possible that functionality from one subsystem may be integrated into others such that one or more of the four subsystems discussed above are eliminated. So, as an example, in another possible implementation shown schematically in FIG. 2, system 219 can be configured to include an input and design module 222 corresponding to all or part of the functions performed by scanning subsystem 21 and design engine 23 of one of the previously described implementations. A customized footwear manufacturing module 227 is adapted to receive suitable output from module 222 to create the requisite footwear, similar to the functions described in manufacturing subsystem 27 of the previous implementation. The intermediary of a virtual last may or may not be applicable to such systems.

Certain quality and design checks can be included in the above-described system, to ensure that the suggested accommodations are appropriate in the resulting product and meet the patients' needs. It is likewise possible that any one of the modules can be the subject of multiple iterations, as different options are tried and different prototypes are created.

The operation of the systems disclosed herein makes use of suitable input devices, whether scanners, cameras, x-ray or other medical imaging systems, pressure plates, keyboards, and the like.

Figure 3:
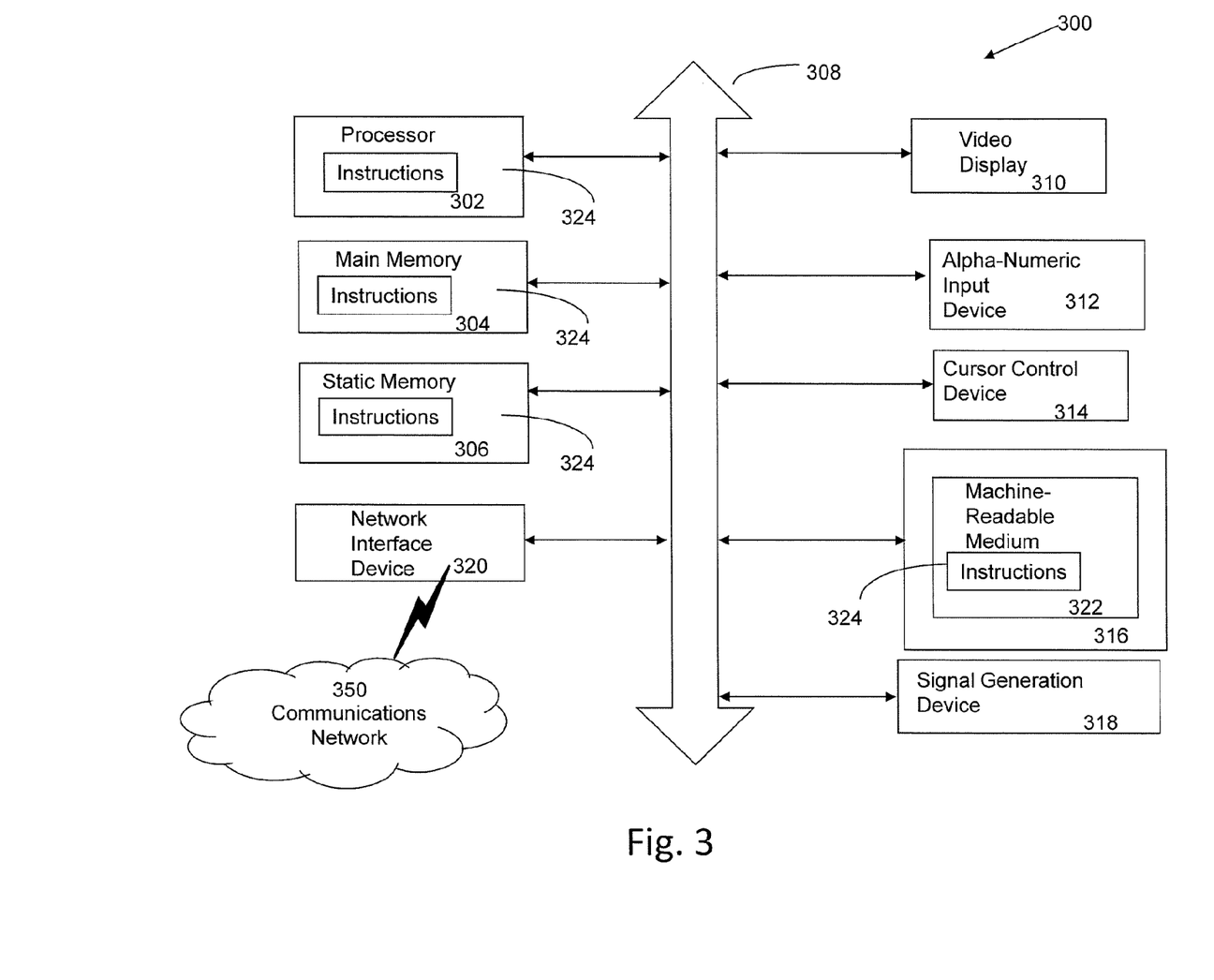
FIG. 3 is a schematic of one possible computer implementation of the present disclosure.

System 19 may be implemented on any suitable computer platform, using either stand-alone or networked architecture. In one version, there may be one or more Lower extremity-specialist scanning stations in communication with a database or other data storage means, one or more servers or processors, either through a local-area or wide-area network. A client-server architecture using the world-wide web may also be used. In the event computer work-stations are involved, whether as stand-alone versions of system 19 or as just housing foot-specialist input subsystems, such workstations may comprise a computer system 300 which includes a processor 302 (e.g., a central processing unit (CPU), a graphics processing unit (GPU, or both), a main memory 34 and a static memory 306, which communicate with each other via a bus 308. The computer system 300 may further include a video display unit 310 (e.g., a liquid crystal display (LCD), a flat panel, a solid state display, or a cathode ray tube (CRT)). The computer system 300 may include an input device 312 (e.g., a keyboard), a cursor control device 314 (e.g., a mouse), a disk drive unit 316, a signal generation device 318 (e.g., a speaker or remote control) and a network interface device 320.

The disk drive unit 316 may include a machine-readable medium 322 on which is stored one or more sets of instructions 324 (e.g., software) embodying any one or more of the methodologies or functions described herein, including those methods illustrated above. The instructions 324 may also reside, completely or at least partially, within the main memory 304, the static memory 306, or within the processor 302, or a combination thereof, during execution thereof by the computer system 300. The main memory 304 and the processor 302 also may constitute machine-readable media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs in the broad sense to include, without limitation, computer coding, microcode, firmware, or other programming, such software running on a computer processor or other microprocessor. Furthermore, software implementations can include distributed processing or component/object distributed processing, parallel processing, or virtual machine processing can also be constructed to implement the methods described herein. The instructions 324 may further be transmitted or received over the communications network 350 via the network interface device 320.

While the machine-readable medium 322 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies of the present disclosure.

The term "machine-readable medium" shall accordingly be taken to include, but not be limited to: solid-state memories such as a memory card or other package that houses one or more read-only (non-volatile) memories, random access memories, or other re-writable (volatile) memories; magneto-optical or optical medium such as a disk or tape; or other self-contained information archive or set of archives is considered a distribution medium equivalent to a tangible storage medium. Accordingly, the disclosure is considered to include any one or more of a machine-readable medium or a distribution medium, as listed herein and including art-recognized equivalents and successor media, in which the software implementations herein are stored.

The illustrations of arrangements described herein are intended to provide a general understanding of the structure of various embodiments, and they are not intended to serve as a complete description of all the elements and features of apparatus and systems that might make use of the structures described herein. Many other arrangements will be apparent to those of skill in the art upon reviewing the above description. Other arrangements may be utilized and derived therefrom, such that structural and logical substitutions and changes may be made without departing from the scope of this disclosure. Accordingly, the specification and drawings are to be regarded in an illustrative rather than a restrictive sense.

The foregoing is provided for purposes of illustrating, explaining, and describing embodiments of this invention. Thus, although specific arrangements have been illustrated and described herein, it should be appreciated that any arrangement calculated to achieve the same purpose may be substituted for the specific arrangement shown. Combinations of the above arrangements, and other arrangements not specifically described herein, will be apparent to those of skill in the art upon reviewing the above description. Therefore, it is intended that the disclosure not be limited to the particular arrangement(s) disclosed herein.

What is claimed is:

1. A computerized system for the automated design and manufacture of patient protective footwear, comprising:
    a scanning subsystem including a user interface and a lower extremity scanner, the scanning subsystem adapted to receive input related to a patient's lower extremity for which protective footwear is to be designed and manufactured;
    a design engine implemented on a computer having programmable memory and at least one processor that executes instructions stored in the programmable memory, wherein the design engine is programmed to process the lower extremity input into a design for the protective footwear, wherein the design engine is programmed to alter the design in response to receiving inputs indicating at least one of the conditions selected from the group consisting of dermatologic conditions, orthopedic conditions, neurological conditions, biomechanical conditions, surgical conditions, and wherein the design engine generates an outputted design in which the one or more conditions are reflected in the outputted design; and
    a computer-aided manufacturing subsystem programmed to receive data related to the outputted design and manufacture the protective footwear corresponding to the outputted design,
    wherein at least one of the design engine and the scanning subsystem includes first suitable programming to generate design data for the protective footwear corresponding to at least one accommodation for a prior toe amputation, and wherein the design data generated by the first suitable programming corresponds to at least one accommodation selected from the group consisting of an addition of insole material to fill voids from the amputation, a modification of materials under unamputated foot portions to relieve foot-related forces due to the amputation, inclusion of at least one of stiffer alternative materials or more flexible alternative materials at a corresponding location on the footwear, such alternate materials corresponding to a gait abnormality related to the amputation.

2. The system of claim 1, further comprising a virtual last creation subsystem for generating a virtual last from the outputted design, the virtual last comprising data suitable for input into the computer-aided manufacturing subsystem.

3. The system of claim 1, wherein at least one of the design engine and the scanning subsystem includes second suitable programming to generate design data for the protective footwear corresponding to at least one accommodation for a prior history selected from the group consisting of an ulceration and a wound in the plantar surface of a second metatarsalphalangeal joint.

4. The system of claim 3, wherein the design data generated by the second suitable programming corresponds to at least one accommodation selected from the group consisting of a substitution of alternate insole materials to account for a loss of elasticity or a lack of impact absorption, inclusion of friction-reducing insole top cover materials, and modification of insole dimensions associated with a location of the wound or ulceration.

5. The system of claim 1, wherein at least one of the design engine and the scanning subsystem is configured to suggest a plurality of modifications to the design in response to receiving data corresponding to a foot condition to be accommodated.

6. The system of claim 5, wherein at least one of the design engine and the scanning subsystem is configured to receive a selection of one of the plurality of modifications to the design, and wherein the programming of the design engine includes instructions to modify the design in response to the selection of the modification.

7. A computerized system for the automated design and manufacture of patient protective footwear, comprising:
    a scanning subsystem including a user interface and a lower extremity scanner, the scanning subsystem adapted to receive input related to a patient's lower extremity for which protective footwear is to be designed and manufactured; and
    a design engine implemented on a computer having programmable memory and at least one processor that executes instructions stored in the programmable memory, wherein the design engine is programmed to process the lower extremity input into a design for the protective footwear, wherein the design engine is programmed to alter the design in response to receiving inputs indicating at least one of the conditions selected from the group consisting of dermatologic conditions, orthopedic conditions, neurological conditions, biomechanical conditions, surgical conditions, and wherein the design engine generates an outputted design in which the one or more conditions are reflected in the outputted design;
    wherein at least one of the design engine and the scanning subsystem includes first suitable programming to generate design data for the protective footwear corresponding to at least one accommodation for a prior toe amputation, and, wherein at least one of the design engine and the scanning subsystem includes further suitable programming to generate design data for the protective footwear corresponding to at least one accommodation for a hammer toe condition.

8. The system of claim 7, wherein the design data generated by the further suitable programming corresponds to at least one accommodation selected from the group consisting of a modification of top cover and vamp of the footwear to be manufactured as a function of dimensions of the forefoot detected by the scanning subsystem, an adjustment of dimensions of the insole as a function of at least one of digital contraction and a condition in dorsal skin, a modification to outsole flexibility, roller-rocker construction, and use of at least one of the following materials: filler, a pad, shear-reducing materials, friction reducing materials, and heat adaptable materials.

9. A computer-implemented method of designing and manufacturing patient protective footwear comprising the steps of:
   scanning a patient's lower extremity to detect dimensions related to the protective footwear to be designed and manufactured;
   receiving inputs indicating at least one of the lower extremity conditions selected from the group consisting of dermatologic conditions, orthopedic conditions, neurological conditions, biomechanical conditions, and surgical conditions
   generating a design in which the one or more conditions corresponding to the inputs received are reflected in the design; and
   manufacturing the protective footwear based on the design, wherein the step of generating a design includes the step of generating design data for the protective footwear corresponding to at least one accommodation for a prior toe amputation, and wherein the step of generating design data includes generating design data corresponding to at least one accommodation selected from the group consisting of an addition of insole material to fill voids from the amputation, a modification of materials under unamputated foot portions to relieve foot-related forces due to the amputation, inclusion of at least one of stiffer alternative materials or more flexible alternative materials at a corresponding location on the footwear, such alternate materials corresponding to a gait abnormality related to the amputation.

10. The method of claim 9, further including the step of creating a virtual last from the design, the virtual last comprising data suitable for input into the step of manufacturing the protective footwear.

11. The method of claim 9, wherein the step of generating a design includes the step of generating design data corresponding to at least one accommodation for a prior history selected from the group consisting of an ulceration and a wound in a plantar surface of a second metatarsal-phalangeal joint.

12. The method of claim 9, wherein the step of generating a design includes the step of generating design data corresponding to at least one accommodation for a hammer toe condition.

13. The method of claim 9, wherein the step of generating a design includes the step of generating a plurality of potential modifications to the design in response to receiving of inputs.

14. The method of claim 13, wherein the step of generating a design includes receiving a selection input a selected one of the plurality of modifications to the design and modifying the design in response to the selection of the modification.

15. The method of claim 9, further comprising the step of determining from the dimensions scanned by the scanning step whether the dimensions detected correspond to any one of a plurality of lower extremity conditions to be accommodated in a footwear design, wherein the step of generating a design, in response to a determination of a condition to be accommodated, further includes the step of modifying potential features of the design to accommodate the detected condition.

* * * * *